(12) United States Patent
Moriguchi

(10) Patent No.: US 10,016,124 B2
(45) Date of Patent: Jul. 10, 2018

(54) DATA PROCESSING METHOD AND OCT APPARATUS

(71) Applicant: KABUSHIKI KAISHA TOPCON, Itabashi-ku (JP)

(72) Inventor: Yoshikiyo Moriguchi, Itabashi-ku (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 236 days.

(21) Appl. No.: 14/879,421

(22) Filed: Oct. 9, 2015

(65) Prior Publication Data

US 2016/0106310 A1 Apr. 21, 2016

(30) Foreign Application Priority Data

Oct. 20, 2014 (JP) .................. 2014-213521

(51) Int. Cl.
| | |
|---|---|
| *G01B 9/02* | (2006.01) |
| *A61B 3/00* | (2006.01) |
| *A61B 3/10* | (2006.01) |
| *A61B 3/12* | (2006.01) |
| *A61B 3/14* | (2006.01) |

(52) U.S. Cl.
CPC .......... *A61B 3/0025* (2013.01); *A61B 3/0083* (2013.01); *A61B 3/102* (2013.01); *A61B 3/12* (2013.01); *A61B 3/14* (2013.01); *G01B 9/02083* (2013.01); *G01B 9/02091* (2013.01)

(58) Field of Classification Search
CPC .................. G01B 9/02004; G01B 9/02091
See application file for complete search history.

(56) References Cited

U.S. PATENT DOCUMENTS

| | | | | |
|---|---|---|---|---|
| 2012/0013914 | A1* | 1/2012 | Kemp .................. | A61B 5/0066 356/479 |
| 2012/0162659 | A1* | 6/2012 | Goldberg ........... | G01N 21/4795 356/479 |
| 2014/0028997 | A1* | 1/2014 | Cable ................. | G01B 9/02091 356/51 |

OTHER PUBLICATIONS

Meng-Tsan Tsai, et al., "Microvascular Imaging Using Swept-Source Optical Coherence Tomography with Single-Channel Acquisition", Applied Physics Express, (4), 2011, 3 pgs.
WooJhon Choi, et al., "Phase-sensitive swept source OCT imaging of the human retina with a VCSEL light source", Optics Letters, vol. 38, (3), 2013, 7 pgs.

* cited by examiner

*Primary Examiner* — Jonathan Hansen
(74) *Attorney, Agent, or Firm* — Oblon, McClelland, Maier & Neustadt, L.L.P.

(57) ABSTRACT

According to one embodiment, a data processing method is used for processing collected data acquired with respect to each A-line by swept-source OCT using a wavelength sweeping light source having a predetermined wavelength sweeping range. The data processing method detects a reference signal assigned in advance to a clock, the wavenumber of which linearly varies along the time axis, in a predetermined wavelength position within the predetermined wavelength sweeping range. Then, the data processing method sequentially performs sampling of the collected data based on the clock with reference to the predetermined wavelength position where the reference signal detected is assigned. Further, the data processing method forms an image of a corresponding A-line based on the sampled collected data.

10 Claims, 8 Drawing Sheets

DATA PROCESSING METHOD AND OCT APPARATUS

CROSS-REFERENCE TO RELATED APPLICATION

This application is based upon and claims the benefit of priority from Japanese Patent Application No. 2014-213521, filed Oct. 20, 2014; the entire contents of which are incorporated herein by reference.

FIELD

Embodiments described herein relate generally to data processing method and an optical coherence tomography (OCT) apparatus for processing data collected by OCT.

BACKGROUND

In recent years, optical coherence tomography (OCT) has been drawing attention. The OCT creates an image representing the exterior or interior structure of an object to be measured using light beams from a laser light source or the like. Unlike X-ray computed tomography (CT), the OCT is not invasive on the human body, and therefore is expected to be applied to the medical field and the biological field, in particular. For example, in the ophthalmological field, apparatuses for forming images of the fundus oculi or the cornea have been in practical use. Such an apparatus using OCT imaging (OCT apparatus) can be used to observe a variety of sites of a subject's eye. In addition, because of the ability to acquire high precision images, the OCT apparatus is applied to the diagnosis of various eye diseases.

Among the OCT apparatuses, regarding those that use Fourier domain OCT imaging, it is known that a fixed pattern noise (FPN) is present in corrected data, and that the FPN may not be completely removed and appear in images, resulting in a reduction in image quality.

Regarding apparatuses that use spectral domain OCT imaging (hereinafter, SD-OCT), FPN can be removed, for example, by calculating the average spectrum in the A-line direction in each irradiation position and subtracting the average spectrum from spectrums measured.

Meanwhile, apparatuses that use swept-source OCT imaging (hereinafter, SS-OCT) are not capable of removing FPN even with the same method as the SD-OCT. Considered as a factor of this is jitter in the time-axis direction between the timing of controlling the light source and the timing of light emission from the light source. Due to the influence of jitter, SS-OCT is considered as unsuitable for imaging with the use of phase information (such as Doppler OCT, Phase Variance OCT, and the like) as compared to SD-OCT.

As for a method to reduce the influence of jitter in SS-OCT, reference may be had to Meng-Tsan Tsai et al, "Microvascular Imaging Using Swept-Source Optical Coherence Tomography with Single-Channel Acquisition" Applied Physics Express 4 (2011), pp. 097001-1 to 097001-3, and WooJhon Choi et al., "Phase-sensitive swept-source optical coherence tomography imaging of the human retina with a vertical cavity surface-emitting laser light source" Optics Letters, vol. 38, No. 3, 2013 Feb. 1, pp. 338-340. These documents disclose a method of removing FPN. According to the method, trigger signals are generated by fiber Bragg grating (FBG), and an image is formed after the phases of interference signals are adjusted with reference to the trigger signals.

However, in this method, the phases of interference signals are adjusted in response to wavenumber clocks for sampling the interference signals besides the trigger signals to thereby reduce the influence of jitter. This leads to the complication of the configuration and control of the apparatus.

SUMMARY

The purpose of the present invention is to provide a method and an apparatus for reducing the influence of jitter with a simple structure in SS-OCT.

According to one aspect of an embodiment, a data processing method is used for processing collected data acquired with respect to each A-line by swept-source OCT using a wavelength sweeping light source having a predetermined wavelength sweeping range. The data processing method detects a reference signal assigned in advance to a clock, the wavenumber of which linearly varies along the time axis, in a predetermined wavelength position within the predetermined wavelength sweeping range. Then, the data processing method sequentially performs sampling of the collected data based on the clock with reference to the predetermined wavelength position where the reference signal detected is assigned. Further, the data processing method forms an image of a corresponding A-line based on the sampled collected data.

According to another aspect of the embodiment, a data processing method is used for processing collected data acquired with respect to each A-line by swept-source OCT using a wavelength sweeping light source having a predetermined wavelength sweeping range. The data processing method performs sampling of the collected data based on a clock, which is assigned in advance a reference signal in a predetermined wavelength position within the predetermined wavelength sweeping range, and the wavenumber of which linearly varies along the time axis. Then the data processing method corrects the phase of the sampled collected data based on the predetermined wavelength position where the reference signal is assigned further, the data processing method forms an image of a corresponding A-line based on the collected data, the phase of which has been corrected.

According to still another aspect of the embodiment, an OCT apparatus is configured to acquire collected data with respect to each A-line by swept-source OCT using a wavelength sweeping light source having a predetermined wavelength sweeping range. The OCT apparatus includes a clock generator, a detector, an acquisition part, and an image forming part. The clock generator is configured to generate a clock, which includes a reference signal in a predetermined wavelength position within the predetermined wavelength sweeping range, and the wavenumber of which linearly varies along the time axis. The detector is configured to detect the reference signal in the clock generated by the clock generator. The acquisition part is configured to sequentially perform sampling of the collected data based on the clock with reference to the predetermined wavelength position where the reference signal detected by the detector is assigned to acquire the collected data. The image forming part is configured to form an image of a corresponding A-line based on the collected data acquired by the acquisition part.

According to still another aspect of the embodiment, an OCT apparatus is configured to acquire collected data with respect to each A-line by swept-source OCT using a wavelength sweeping light source having a predetermined wavelength sweeping range. The OCT apparatus includes a clock generator, an acquisition part, and an image forming part. The clock generator is configured to generate a clock, which includes a reference signal in a predetermined wavelength position within the predetermined wavelength sweeping range, and the wavenumber of which linearly varies along the time axis. The acquisition part is configured to perform sampling of the collected data based on the clock generated by the clock generator to acquire the collected data. The image forming part is configured to correct the phase of the collected data acquired by the acquisition part based on the predetermined wavelength position where the reference signal is assigned, and form an image of a corresponding A-line based on the collected data, the phase of which has been corrected.

According to the embodiment, in SS-OCT, the influence of jitter can be reduced with a simple structure.

DETAILED DESCRIPTION

Figure 1:
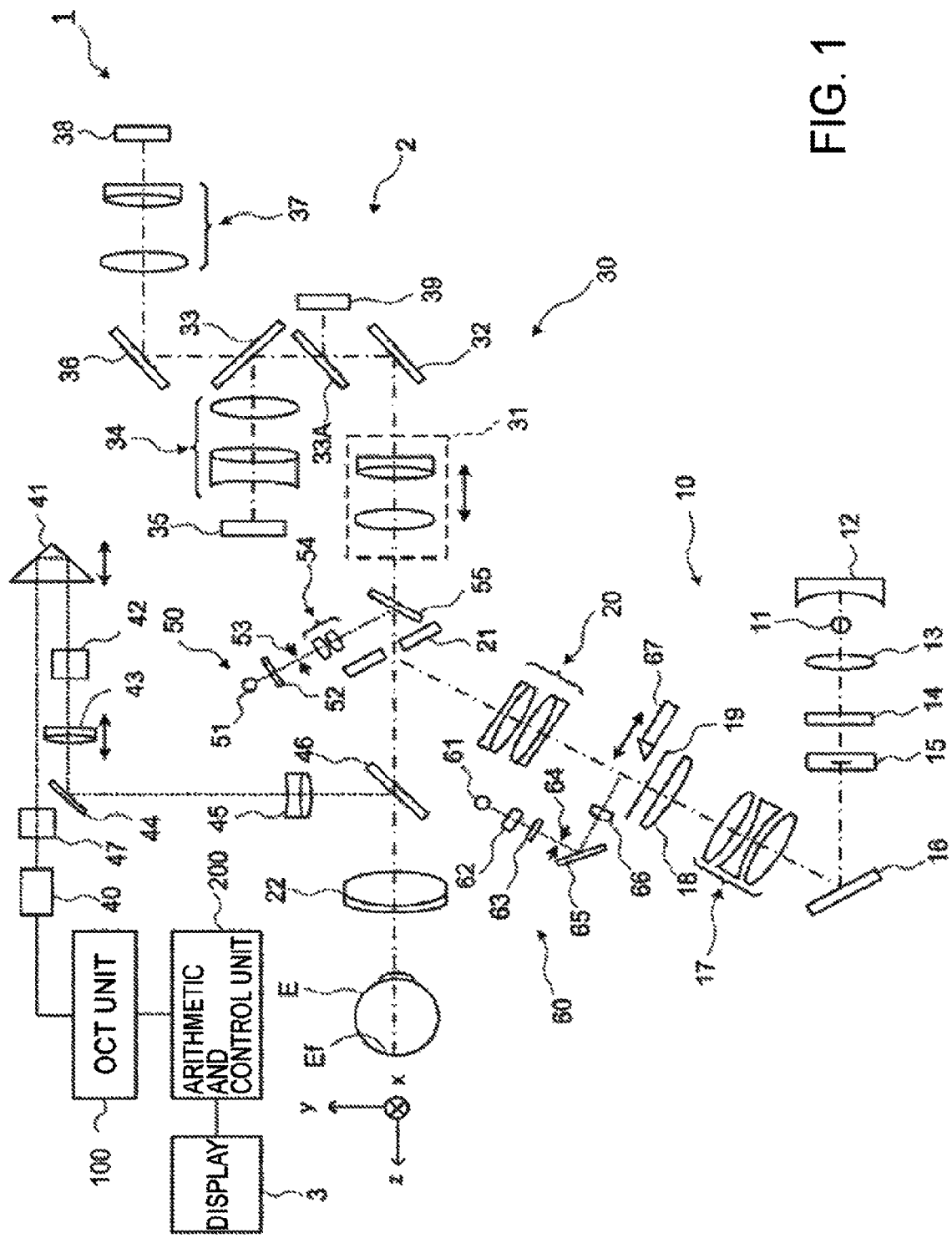
FIG. 1 is a schematic diagram illustrating an example of the configuration of an OCT apparatus according to an embodiment.

Referring now to the drawings, a detailed description is given of an OCT apparatus according to an embodiment. The OCT apparatus of the embodiment creates cross sectional images and three-dimensional images of an object to be measured using OCT imaging technology. The image acquired through OCT may sometimes be herein referred to as "OCT image". In addition, measurement for forming the OCT image may sometimes be herein referred to as "OCT measurement". The contents of the documents cited herein are incorporated by reference into the embodiment as appropriate.

Assuming a biological eye (subject's eye, fundus) as an object to be measured, the following embodiment describes a fundus imaging apparatus that uses an OCT apparatus configured to perform OCT measurement of the fundus using swept-source OCT imaging. The fundus imaging apparatus of the embodiment is capable of acquiring OCT images of the fundus and also fundus images by photographing the fundus. Although the apparatus described in this embodiment is formed of a combination of an OCT apparatus and a fundus camera (retinal camera), the OCT apparatus of the embodiment may be combined with a fundus imaging apparatus other than a fundus camera. Examples of the fundus imaging apparatus include scanning laser ophthalmoscopes (SLO), slit lamp, ophthalmic operating microscope, photocoagulator, and the like. The configuration of the embodiment may be applied to an OCT apparatus alone.

[Configuration]

As illustrated in FIGS. 1 to 4, a fundus imaging apparatus 1 includes a fundus camera unit 2, an OCT unit 100, and an arithmetic and control unit 200. The fundus camera unit 2 has almost the same optical system as that of a conventional fundus camera. The OCT unit 100 is provided with an optical system for obtaining an OCT image of a fundus. The arithmetic and control unit 200 is provided with a computer that performs various arithmetic processes, control processes, and the like.

[Fundus Camera Unit]

The fundus camera unit 2 illustrated in FIG. 1 is provided with an optical system for obtaining a front image (fundus image) of a fundus Ef of an eye E viewed from the cornea side. Examples of the fundus image include an observation image, a photographic image, and the like. The observation image is, for example, a monochrome moving image formed at a prescribed frame rate using near-infrared light. The photographic image is, for example, a color image captured by flashing visible light, or a monochrome still image using near-infrared light or visible light as illumination light. The fundus camera unit 2 may be configured to be capable of acquiring other types of images such as a fluorescein angiography image, an indocyanine green fluorescent image, and an autofluorescent image.

The fundus camera unit 2 is provided with a jaw holder and a forehead rest for supporting the face of the subject. The fundus camera unit 2 is further provided with an illumination optical system 10 and an imaging optical system 30. The illumination optical system 10 irradiates the fundus Ef with illumination light. The imaging optical system 30 guides the illumination light reflected from the fundus to an imaging device (CCD image sensors 35 and 38, sometimes simply referred to as "CCD"). Besides, the imaging optical system 30 guides measurement light from the OCT unit 100 to the fundus Ef, and guides the measurement light returned from the fundus Ef to the OCT unit 100.

An observation light source 11 of the illumination optical system 10 includes, for example, a halogen lamp. The light (observation illumination light) output from the observation light source 11 is reflected by a reflection mirror 12 having a curved reflective surface, and becomes near-infrared light after passing through a visible cut filter 14 via a condenser lens 13. Further, the observation illumination light is once converged near an imaging light source 15, reflected by a mirror 16, and passes through relay lenses 17 and 18, a diaphragm 19, and a relay lens 20. Then, the observation illumination light is reflected on the periphery of an aperture mirror 21 (the region surrounding an aperture), penetrates a dichroic mirror 46, and is refracted by an objective lens 22, thereby illuminating the fundus Ef. Note that a light emitting diode (LED) may be used as the observation light source.

The observation illumination light reflected from the fundus (fundus reflection light) is refracted by the objective lens 22, penetrates through the dichroic mirror 46, passes through the aperture formed in the center region of the aperture mirror 21, penetrates through a dichroic mirror 55, travels through a focusing lens 31, and is reflected by a mirror 32. Further, the fundus reflection light passes through a half mirror 33A, is reflected by a dichroic mirror 33, and forms an image on the light receiving surface of the CCD image sensor 35 by a condenser lens 34. The CCD image sensor 35 detects the fundus reflection light at a preset frame rate, for example. An image (observation image) based on the fundus reflection light detected by the CCD image sensor 35 is displayed on a display 3. Note that when the imaging optical system 30 is focused on an anterior eye segment of the eye E, an observation image of the anterior eye segment of the eye E is displayed.

The imaging light source 15 is formed by a xenon lamp, for example. The light (imaging illumination light) output from the imaging light source 15 is guided to the fundus Ef through a route as with the observation illumination light. The imaging illumination light reflected from the fundus (fundus reflection light) is guided to the dichroic mirror 33 through the same route as that of the observation illumination light, passes through the dichroic mirror 33, is reflected by a mirror 36, and forms an image on the light receiving surface of the CCD image sensor 38 by a condenser lens 37. An image (photographic image) based on the fundus reflection light detected by the CCD image sensor 38 is displayed on the display 3. Note that the same device or different devices may be used to display an observation image and a photographic image. Further, when similar photographing is performed by illuminating the eye E with infrared light, an infrared photographic image is displayed. Besides, an LED may be used as the imaging light source.

A liquid crystal display (LCD) 39 displays a fixation target, a visual target for measuring visual acuity, and the like. The fixation target is a visual target for fixating the eye E, and is used on the occasion of fundus photographing, OCT measurement, and the like.

Part of the light output from the LCD 39 is reflected by the half mirror 33A, reflected by the mirror 32, travels through the focusing lens 31 and the dichroic mirror 55, passes through the aperture of the aperture mirror 21, penetrates through the dichroic mirror 46, and is refracted by the objective lens 22, thereby being projected onto the fundus Ef.

By changing the display position of the fixation target on the screen of the LCD 39, the fixation position of the eye E can be changed. Examples of the fixation position of the eye E include, as with a conventional fundus camera, a position for acquiring an image centered on the macula of the fundus Ef, a position for acquiring an image centered on the optic papilla, a position for acquiring an image centered on the fundus center between the macula and the optic papilla, and the like. In addition, the display position of the fixation target may be arbitrarily changed.

Further, as with a conventional fundus camera, the fundus camera unit 2 is provided with an alignment optical system 50 and a focus optical system 60. The alignment optical system 50 generates a target (alignment indicator) for position matching (alignment) of the optical system of the apparatus with respect to the eye E. The focus optical system 60 generates a target (split target) for adjusting the focus with respect to the eye E.

Light (alignment light) output from LED 51 of the alignment optical system 50 travels through diaphragms 52 and 53 and a relay lens 54, is reflected by the dichroic mirror 55, passes through the aperture of the aperture mirror 21, penetrates through the dichroic mirror 46, and is projected onto the cornea of the eye E by the objective lens 22.

The alignment light reflected from the cornea (cornea reflection light) travels through the objective lens 22, the dichroic mirror 46 and the abovementioned aperture. Part of the cornea reflection light penetrates through the dichroic mirror 55, passes through the focusing lens 31, is reflected by the mirror 32, penetrates through the half mirror 33A, is reflected by the dichroic mirror 33, and is projected onto the light receiving surface of the CCD image sensor 35 by the condenser lens 34. An image (alignment indicator) captured by the CCD image sensor 35 is displayed on the display 3 together with the observation image. A user can perform alignment in the same way as a conventional fundus camera. Further, alignment may be performed in such a way that the arithmetic and control unit 200 analyzes the position of the alignment indicator and moves the optical system (automatic alignment).

To conduct focus adjustment, the reflective surface of a reflection rod 67 is arranged in a slanted position on the optical path of the illumination optical system 10. Light (focus light) output from LED 61 of the focus optical system 60 passes through a relay lens 62, is split into two light fluxes by a split target plate 63, passes through a two-hole diaphragm 64, is reflected by a mirror 65, and is reflected after once forming an image on the reflective surface of the reflection rod 67 by a condenser lens 66. Further, the focus light travels through the relay lens 20, is reflected by the aperture mirror 21, penetrates through the dichroic mirror 46, and is refracted by the objective lens 22, thereby being projected onto the fundus Ef.

The focus light reflected from the fundus passes through the same route as the cornea reflection light of the alignment light and is detected by the CCD image sensor 35. An image (split target) captured by the CCD image sensor 35 is displayed on the display 3 together with an observation image. As with a conventional case, the arithmetic and control unit 200 analyzes the position of the split target, and moves the focusing lens 31 and the focus optical system 60 for focusing (automatic focusing). The user can manually perform focus adjustment while visually checking the split target.

The dichroic mirror 46 branches the optical path for OCT measurement (OCT optical path) from the optical path for fundus photography. The dichroic mirror 46 reflects light of wavelengths used in OCT measurement and transmits light for fundus photography. On the OCT optical path, a collimator lens unit 40, a dispersion compensation member 47, an optical path length changing part 41, a galvano-scanner 42, a focusing lens 43, a mirror 44, and a relay lens 45 are provided in this order from the OCT unit 100.

The dispersion compensation member 47 is arranged on the OCT optical path between the collimator lens unit 40 and the optical path length changing part 41. The dispersion compensation member 47 functions as a dispersion compensator to match the dispersion properties of measurement light and reference light generated in the OCT unit 100.

The optical path length changing part 41 is movable in the direction indicated by the arrow in FIG. 1, thereby changing the length of the OCT optical path. The change in the optical path length is used for correction of the optical path length in accordance with the axial length of the eye E, adjustment of the interference state, and the like. The optical path length changing part 41 includes, for example, a corner cube and a mechanism for moving it.

The galvano-scanner 42 changes the travelling direction of light (measurement light LS) travelling along the OCT optical path. Thereby, the fundus Ef can be scanned with the measurement light LS. The galvano-scanner 42 includes, for example, a galvanometer mirror for scanning the measurement light LS in the x direction, a galvanometer mirror for scanning in the y direction, and a mechanism configured to independently drive them. Accordingly, the measurement light LS can be deflected in any direction on the xy plane.

[OCT Unit]

Figure 2:
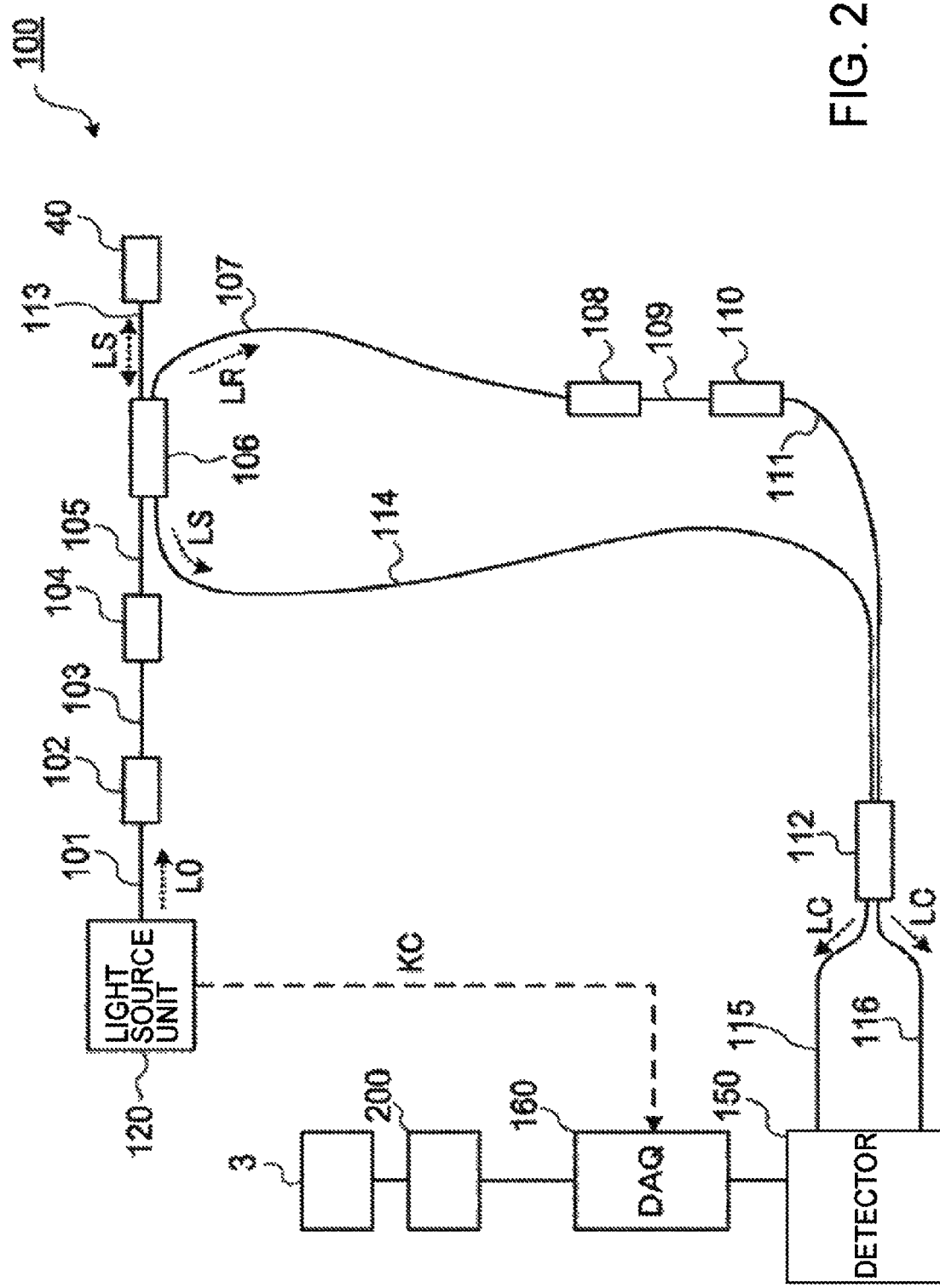
FIG. 2 is the schematic diagram illustrating an example of the configuration of the OCT apparatus of the embodiment.

With reference to FIG. 2, a description is given of an example of the configuration of the OCT unit 100. The OCT unit 100 is provided with an optical system for acquiring an OCT image of the fundus Ef. The optical system has a similar configuration to that of conventional swept-source OCT. That is, the optical system includes an interference optical system configured to split light from a wavelength sweeping light source (wavelength tunable light source) into measurement light and reference light, make the measurement light returned from the fundus Ef and the reference light having passed through a reference optical path interfere with each other to generate interference light, and detect the interference light. The detection result (detection signal) of the interference light obtained by the interference optical system is a signal indicating the spectra of the interference light and is sent to the arithmetic and control unit 200.

Note that, as with a general swept-source OCT apparatus, a light source unit 120 includes a wavelength sweeping light source (wavelength tunable light source) capable of sweeping (varying) the wavelength of output light within a predetermined wavelength sweeping range. The light source unit 120 temporally changes the output wavelength within near-infrared wavelength bands not visible to the human eye.

The light L0 output from the light source unit 120 is guided to an attenuator 102 through an optical fiber 101, and the light amount thereof is adjusted under the control of the arithmetic and control unit 200. The light L0, the amount of which has been adjusted by the attenuator 102, is guided to a polarization controller 104 through an optical fiber 103, and the polarization state thereof is adjusted. The polarization controller 104 is configured to, for example, apply external stress to the optical fiber 103 in a looped shape, thereby adjusting the polarization state of the light L0 guided in the optical fiber 103.

The light L0, the polarization state of which has been adjusted by the polarization controller 104, is guided to a fiber coupler 106 through an optical fiber 105, and split into measurement light LS and reference light LR.

The reference light LR is guided to an attenuator 108 through an optical fiber 107, and the light amount thereof is adjusted under the control of the arithmetic and control unit 200. The reference light LR, the amount of which has been adjusted by the attenuator 108, is guided to a polarization controller 110 through an optical fiber 109, and the polarization state thereof is adjusted.

For example, the polarization controller 110 has the same configuration as that of the polarization controller 104. The reference light LR, the polarization state of which has been adjusted by the polarization controller 110, is guided to a fiber coupler 112 through an optical fiber 111.

The measurement light LS generated by the fiber coupler 106 is guided through an optical fiber 113 and collimated into a parallel light flux by the collimator lens unit 40. Further, the collimated measurement light LS arrives at the dichroic mirror 46 via the dispersion compensation member 47, the optical path length changing part 41, the galvano-scanner 42, the focusing lens 43, the mirror 44, and the relay lens 45. Subsequently, the measurement light LS is reflected by the dichroic mirror 46, refracted by the objective lens 22, and projected onto the fundus Ef. The measurement light LS is scattered and reflected at various depth positions of the fundus Ef. Back-scattered light (returned light) of the measurement light LS from the fundus Ef reversely travels along the same path as the outward path and is guided to the fiber coupler 106, thereby arriving at the fiber coupler 112 through an optical fiber 114.

The fiber coupler 112 causes the measurement light LS incident via the optical fiber 114 and the reference light LR incident via the optical fiber 111 to combine (interfere) with each other to generate interference light. The fiber coupler 112 splits the interference light between the measurement light LS and the reference light LR at a predetermined splitting ratio (e.g., 50:50) to generate a pair of interference light beams LC. The pair of interference light beams LC output from the fiber coupler 112 is guided to a detector 150 through optical fibers 115 and 116.

The detector 150 includes a pair of photodetectors each configured to detect corresponding one of the pair of interference light beams LC. The detector 150 may be balanced photodiodes (BPDs) that output the difference between detection signals obtained by the photodetectors. The detector 150 sends the detection signal (detection result) as an interference signal to a data acquisition system (DAQ) 160. The detection signal (detection result) obtained by the detector 150 corresponds to an example of "collected data" of the embodiment.

The DAQ 160 is fed with a wavenumber clock KC from the light source unit 120. The wavenumber clock KC includes a reference signal in a predetermined wavelength position within a predetermined wavelength sweeping range of the wavelength sweeping light source. The wavenumber of the wavenumber clock KC linearly varies along the time axis. In this embodiment, the wavenumber clock KC is optically generated by a clock generating optical system based on the light from the wavelength sweeping light source. The phrase "optically generated" as used herein means to be generated mainly by optical members without the influence of jitter. The DAQ 160 acquires the detection signals obtained by the detector 150 based on the wavenumber clock KC.

Figure 3:
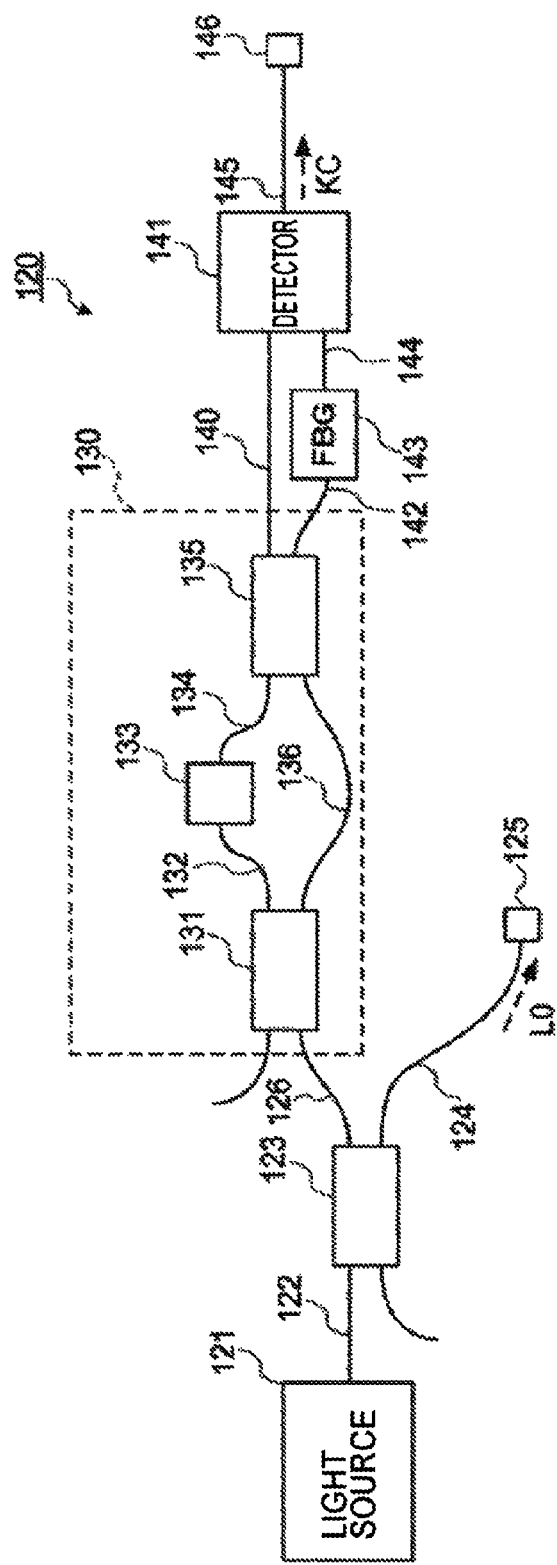
FIG. 3 is a schematic diagram illustrating an example of the configuration of the OCT apparatus of the embodiment.

FIG. 3 illustrates an example of the configuration of the light source unit 120. In the light source unit 120, a light source 121 as a wavelength sweeping light source performs wavelength sweeping within a wavelength sweeping range between a predetermined sweeping start wavelength and a predetermined sweeping end wavelength. The light emitted from the light source 121 is guided to a light splitter 123 through an optical fiber 122. The light splitter 123 splits the light from the light source 121 at a predetermined splitting ratio (e.g., 95:5), and thereby generates light L0 (95%) and branch light (5%). The light L0 is emitted from an emitting end 125 via an optical fiber 124. The branch light is guided to a clock generating optical system 130 through an optical fiber 126.

The clock generating optical system 130 optically generates a wavenumber clock from the branch light. Specifically, the branch light is guided to a light splitter 131 through the optical fiber 126. The light splitter 131 further splits the branch light at a predetermined splitting ratio (e.g., 50:50) to generate a pair of sub-branch light beams. One of the sub-branch light beams generated by the light splitter 131 is guided to a delay optical element 133 through an optical fiber 132. The delay optical element 133 delays the light guided through the optical fiber 132 by a predetermined optical path length. The light delayed by the delay optical element 133 is guided to a fiber coupler 135 through an optical fiber 134. The other sub-branch light beam is guided to the fiber coupler 135 through an optical fiber 136. The fiber coupler 135 causes the pair of light beams incident via the optical fibers 134 and 136 to combine (interfere) with each other to generate interference light. The fiber coupler 135 splits the interference light at a predetermined splitting ratio (e.g., 50:50) to generate a pair of interference light beams. The pair of interference light beams generated by the fiber coupler 135 becomes a clock, the wavenumber of which linearly varies along the time axis. One of the interference light beams output from the fiber coupler 135 is guided to a detector 141 through an optical fiber 140. The other interference light beam output from the fiber coupler 135 is guided to an FBG 143 through an optical fiber 142.

The FBG 143 reflects only predetermined wavelength components of the light beam guided through the optical fiber 142, and transmits the other others components. The FBG 143 is, for example, an optical element fabricated such that the refractive index of the core of the optical fiber varies in the longitudinal direction in a predetermined grating cycle. When the interference light is incident on the FBG 143, only those having a Bragg wavelength corresponding to the grating cycle are reflected, and those having other wavelength components transmit therethrough. Accordingly, if fabricated such that the refractive index of the core of the optical fiber varies in a predetermined grating cycle corresponding to the Bragg wavelength (predetermined wavelength), the FBG 143 reflects only wavelength components of the Bragg wavelength. In the FBG 143, the Bragg wavelength is adjusted to reflect light having wavelength components in a predetermined wavelength position within a predetermined wavelength sweeping range of the wavelength sweeping light source. Examples of the predetermined wavelength position include a wavelength position (reference wavelength position) closer to the sweeping start wavelength than to the sweeping end wavelength of the light source 121. This wavelength position (the reference wavelength position) may be in the vicinity of the boundary of the imaging range as the range of wavelength positions used to form an image within the wavelength sweeping range of the light source 121, or may be outside the imaging range. This facilitates to distinguish the reference signal from the interference signal used to form an image. Thus, the influence of the reference signal can be eliminated upon imaging.

The light having transmitted through the FBG 143 is guided to the detector 141 through an optical fiber 144. The detector 141 may include, for example, BPDs. The detector 141 detects a pair of interference light beams, one of which has transmitted through the FBG 143. Thereby, the detector 141 optically generates a wavenumber clock KC, to which the reference signal is assigned as a trigger signal in a predetermined wavelength position, and the wavenumber of which linearly varies along the time axis. The wavenumber clock KC is output from an emitting end 146 via an optical fiber 145. By optically generating a wavenumber clock in this manner, it is possible to obtain the wavenumber clock KC not affected by jitter.

Incidentally, in FIG. 3, the detector 141 may be a photo diode (PD). The PD is arranged to detect only an interference light beam having transmitted through the FBG 143 and guided through the optical fiber 144 from the pair of interference light beams generated by the fiber coupler 135. In this case, the FBG 143 may be inserted in any one of the optical fibers 126, 132, 134, and 136.

Figure 4:
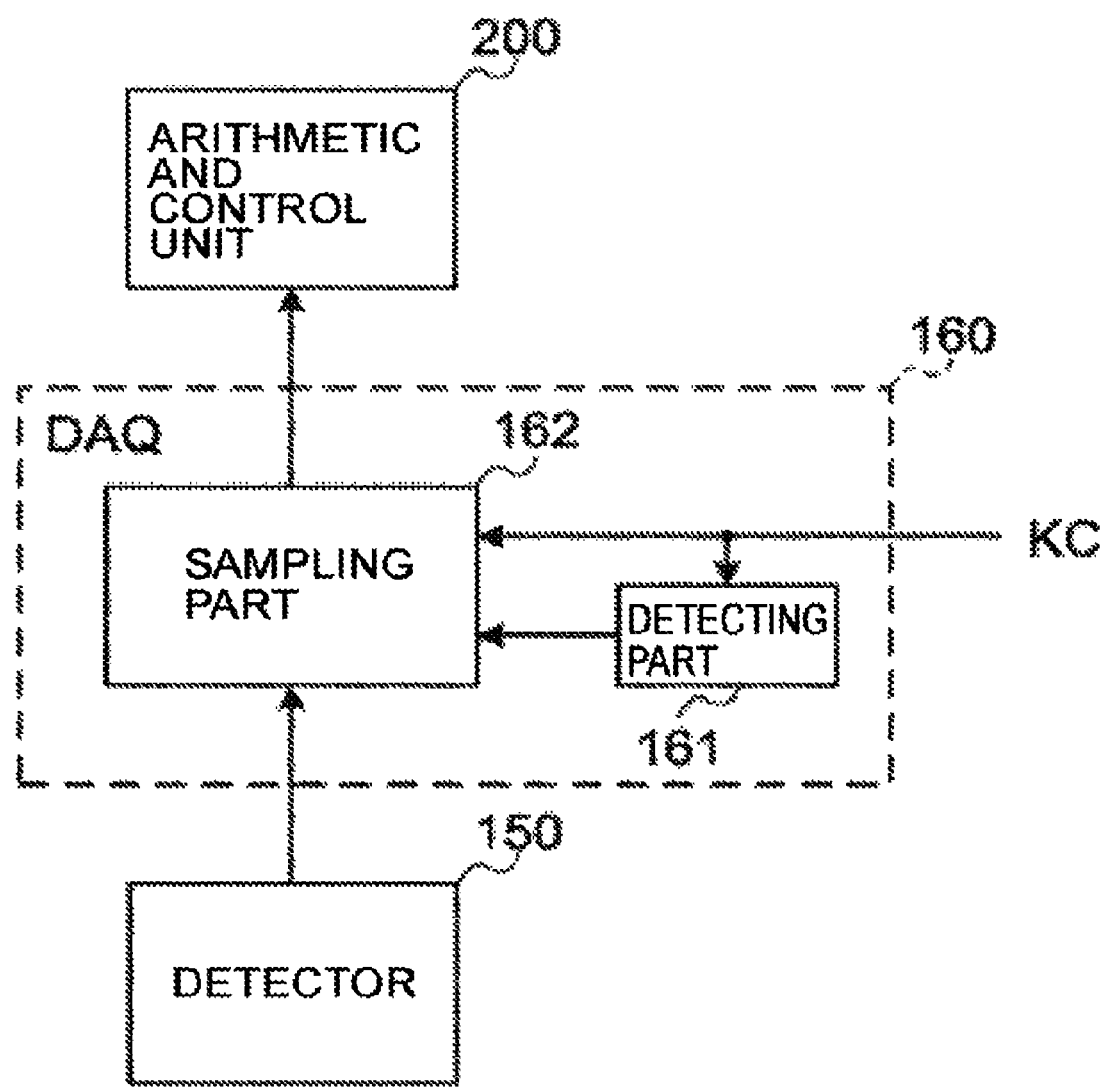
FIG. 4 is a schematic diagram illustrating an example of the configuration of the OCT apparatus of the embodiment.

FIG. 4 is a block diagram illustrating an example of the configuration of the DAQ 160 of the embodiment. In addition to the DAQ 160, FIG. 4 also illustrates the detector 150 and the arithmetic and control unit 200. The DAQ 160 includes a detecting part 161 and a sampling part 162. The detecting part 161 detects the reference signal included in the wavenumber clock KC. This enables the detecting part 161 to specify the wavelength position in the wavenumber clock KC where the reference signal is assigned. The sampling part 162 sequentially performs the sampling of detection signals obtained by the detector 150 based on the wavenumber clock KC with reference to the predetermined wavelength position where the reference signal detected by the detecting part 161 is assigned.

Figure 5:
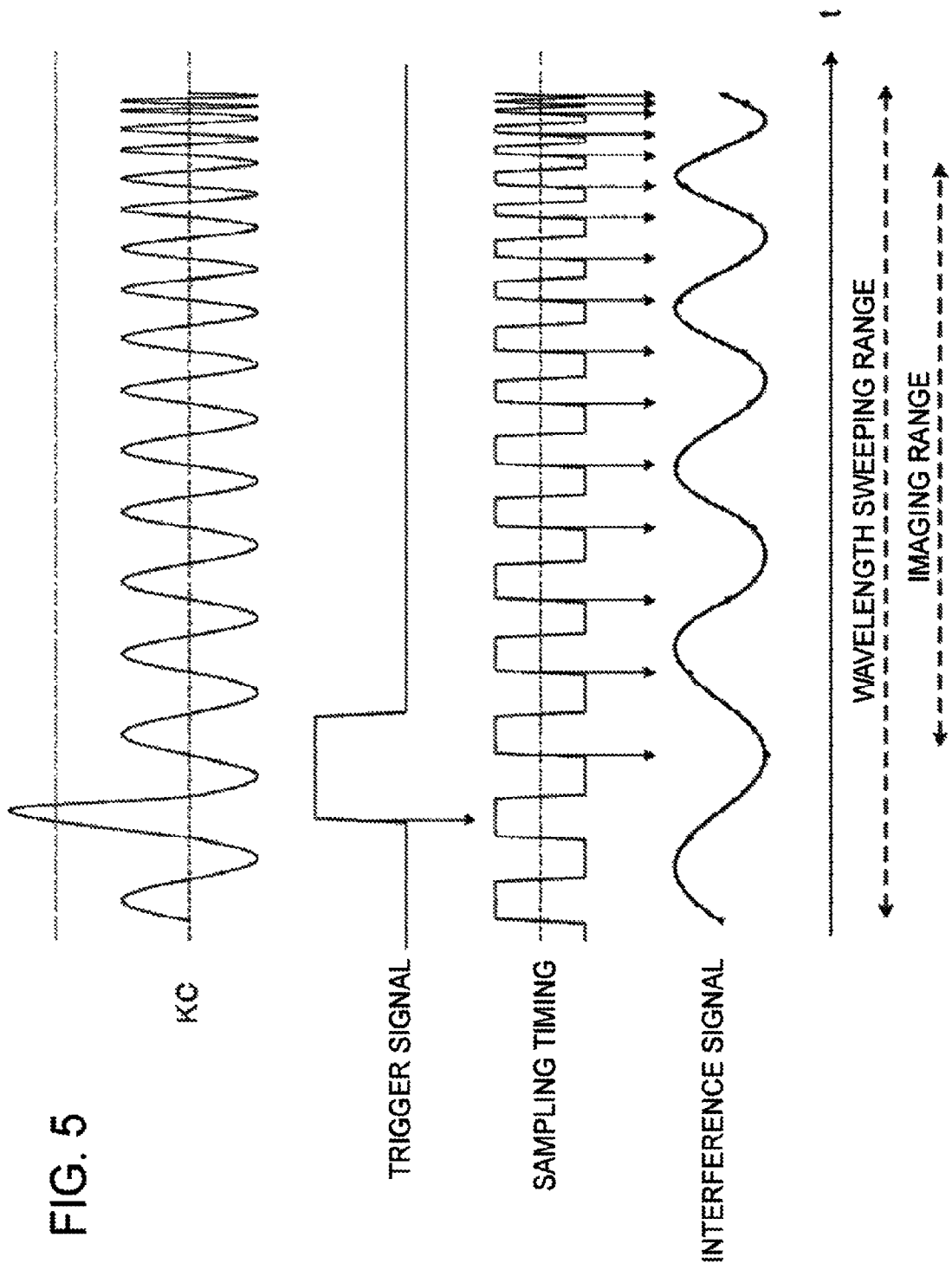
FIG. 5 is an explanatory diagram for explaining the operation of the OCT apparatus of the embodiment.

FIG. 5 illustrates an example of the waveforms of the wavenumber clock KC, the trigger signal, the sampling timing based on the wavenumber clock, and the interference signal (detection signal obtained by the detector 150). In FIG. 5, the horizontal axis represents the time axis, while the vertical axis represents signal intensity.

The detecting part 161 detects, for example, the reference signal assigned to a wavelength position corresponding to the timing of the rising edge of a conventional trigger signal. For example, the detecting part 161 may be configured to detect the reference signal by detecting whether the wave height or amplitude of the wavenumber clock is equal to or above a predetermined threshold. Alternatively, the detecting part 161 may be configured to detect the reference signal by detecting the peak of the wavenumber clock. In addition, the detecting part 161 may be configured to calculate the correlation value between a reference wavenumber clock and the wavenumber clock KC received from the light source unit 120 to detect the reference signal based on the correlation value. Besides, the detecting part 161 may be configured to search for the reference signal in a predetermined wavelength range including the Bragg wavelength of the FBG 143 as a detection range to increase the detection accuracy. The sampling part 162 may be configured to start the sampling of the interference light from a specific wavelength position behind the predetermined wavelength position (reference wavelength position) where the reference signal detected by the detecting part 161 is assigned. With this, the specific wavelength position may be used as the start position of the imaging range. Thus, the reference signal can be assigned to the clock without affecting the image quality. The DAQ 160 sends the detection signals sampled by the sampling part 162 to the arithmetic and control unit 200.

The arithmetic and control unit 200 applies Fourier transform and the like to the spectral distribution based on the detection signals obtained by the detector 150 with respect to each series of wavelength scanning (with respect to each A-line), for example, thereby forming a cross sectional image. The arithmetic and control unit 200 displays the image on the display 3.

Although a Michelson interferometer is employed in this embodiment, it is possible to employ any type of interferometer such as a Mach-Zehnder interferometer as appropriate.

[Arithmetic and Control Unit]

Described below is an example of the configuration of the arithmetic and control unit 200. The arithmetic and control unit 200 analyzes the detection signals fed from the detector 150 to form an OCT image of the fundus Ef. The arithmetic process for this is the same as that of a conventional swept-source OCT.

Further, the arithmetic and control unit 200 controls the fundus camera unit 2, the display 3, and the OCT unit 100. For example, the arithmetic and control unit 200 displays an OCT image of the fundus Ef on the display 3.

Further, as the control of the fundus camera unit 2, the arithmetic and control unit 200 controls: the operations of the observation light source 11, the imaging light source 15 and the LEDs 51 and 61; the operation of the LCD 39; the movements of the focusing lenses 31 and 43; the movement of the reflection rod 67; the movement of the focus optical system 60; the movement of the optical path length changing part 41; the operation of the galvano-scanner 42; and the like.

Further, as the control of the OCT unit 100, the arithmetic and control unit 200 controls: the operation of the light source unit 120; the operation of the detector 150; the operations of the attenuators 102 and 108; the operations of the polarization controllers 104 and 110; the operation of the detector 141; the operation of the DAQ 160 (the detecting part 161 and the sampling part 162); the acquisition of collected data from the DAQ 160; and the like.

The arithmetic and control unit 200 includes a microprocessor, a random access memory (RAM), a read-only memory (ROM), a hard disk drive, a communication interface, and the like, as in a conventional computer. The storage device such as a hard disk drive stores computer programs for controlling the fundus imaging apparatus 1. The arithmetic and control unit 200 may be provided with various types of circuit boards, such as a circuit board for forming an OCT image. The arithmetic and control unit 200 may further include an operation device (input device) such as a keyboard and a mouse, and a display such as LCD.

The fundus camera unit 2, the display 3, the OCT unit 100, and the arithmetic and control unit 200 may be integrally provided (i.e., in a single case), or they may be distributed to two or more cases.

[Control System]

Figure 6:
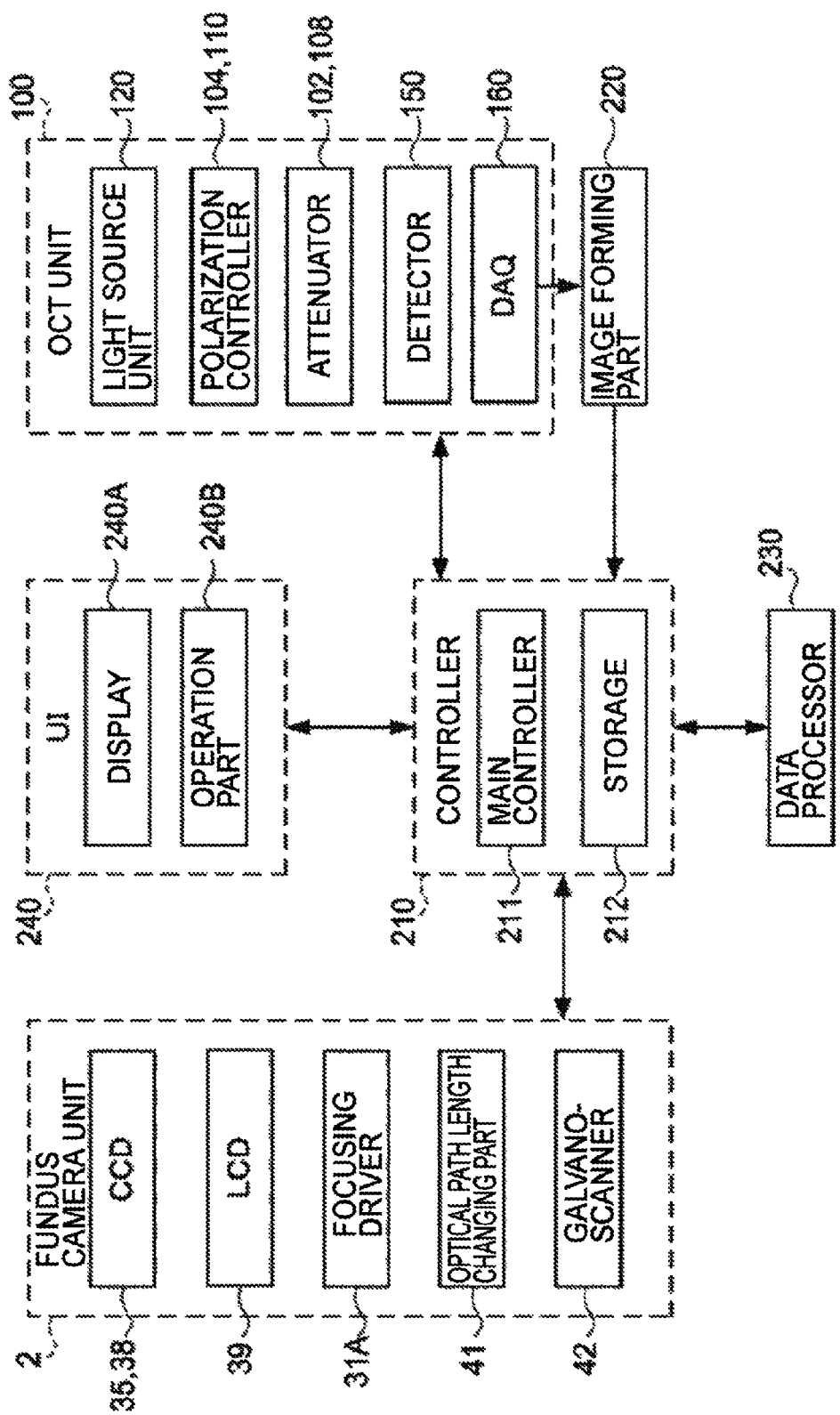
FIG. 6 is a functional block diagram illustrating an example of the configuration of the OCT apparatus of the embodiment.

The configuration of a control system of the fundus imaging apparatus 1 is described with reference to FIG. 6.

(Controller)

A controller 210 is the center of the control system of the fundus imaging apparatus 1. The controller 210 includes, for example, the aforementioned microprocessor, RAM, ROM, hard disk drive, communication interface, and the like. The controller 210 is provided with a main controller 211 and a storage 212.

(Main Controller)

The main controller 211 performs various types of controls mentioned above. In particular, the main controller 211 controls a focusing driver 31A, the optical path length changing part 41, and the galvano-scanner 42 of the fundus camera unit 2, as well as the light source unit 120 (including the detector 141 therein), the polarization controllers 104 and 110, the attenuators 102 and 108, the detector 150, and the DAQ 160 of the OCT unit 100.

The focusing driver 31A moves the focusing lens 31 in the optical axis direction. Thereby, the focus position of the imaging optical system 30 is changed. Note that the main controller 211 can three-dimensionally move the optical system arranged in the fundus camera unit 2 by controlling an optical system driver (not illustrated). This control is used in alignment and tracking. Tracking is the process of moving the optical system of the apparatus in accordance with the movement of the eye E. To perform tracking, alignment and focusing are performed in advance. Tracking is the function of maintaining a good positional relationship with proper alignment and focus by moving the optical system of the apparatus in real time according to the position and orientation of the eye E based on a moving image (observation image) of the eye E.

The main controller 211 is capable of controlling the detection operation of the detecting part 161 of the DAQ 160 by, for example, changing the threshold level for detecting the reference signal or the like. The main controller 211 performs the process of writing data to and reading data from the storage 212.

(Storage)

The storage 212 stores various types of data. Examples of the data stored in the storage 212 include image data of an OCT image, image data of a fundus image, and eye information. The eye information includes information related to a subject such as patient ID and name, information related to the subject's eye such as identification information of left eye/right eye, and the like. The storage 212 further stores various types of computer programs and data to run the fundus imaging apparatus 1.

(Image Forming Part)

An image forming part 220 forms image data of a cross sectional image of the fundus Ef based on collected data acquired by the DAQ 160. That is, the image forming part 220 forms an image of the eye E based on the detection results of interference light collected by SS-OCT. As with a conventional swept-source OCT, this process includes noise removal (noise reduction), filtering, fast Fourier transform (FFT), and the like.

The image forming part 220 includes, for example, the aforementioned circuit board. Note that "image data" and "image" based thereon may be herein treated in the same way.

In this embodiment, the sampling of detection signals obtained by the detector 150 is performed with reference to the predetermined wavelength position where the reference signal is assigned within the predetermined wavelength sweeping range of the wavelength sweeping light source for each A-line. The image forming part 220 forms an image of a corresponding A-line based on collected data acquired by the sampling. With this, an image can be formed based on the collected data where the influence of jitter has been removed. Thus, the image formed by the image forming part 220 is not affected by jitter.

(Data Processor)

A data processor 230 performs various types of image processing and analysis on an image formed by the image forming part 220. For example, the data processor 230 performs various correction processes such as luminance correction and dispersion compensation of an image. Further, the data processor 230 performs various types of image processing and analysis on an image (fundus image, anterior eye image, etc.) obtained by the fundus camera unit 2. For example, the data processor 230 analyzes a moving image of the anterior segment of the eye E to obtain the position and orientation of the eye E during tracking.

The data processor 230 performs known image processing such as an interpolation process for interpolating pixels between cross sectional images, thereby forming image data of a three-dimensional image of the fundus Ef. The image data of a three-dimensional image refers to image data in which the positions of pixels are defined by the three-dimensional coordinates. The image data of a three-dimensional image is, for example, image data composed of three-dimensional arrays of voxels. This image data is referred to as volume data, voxel data, or the like. For displaying an image based on the volume data, the data processor 230 performs a rendering process (such as volume rendering, maximum intensity projection (MIP), etc.) on the volume data to form image data of a pseudo three-dimensional image taken from a specific view direction. This pseudo three-dimensional image is displayed on a display 240A or the like.

The data processor 230 may form the stack data of a plurality of cross sectional images as the image data of a three-dimensional image. The stack data is image data obtained by three-dimensionally arranging a plurality of cross sectional images acquired along a plurality of scan lines based on the positional relationship of the scan lines. In other words, the stack data is image data obtained by expressing a plurality of cross sectional images originally defined by their individual two-dimensional coordinate systems by a single three-dimensional coordinate system (i.e., embedding the images in a single three-dimensional space).

The data processor 230 that functions as described above includes, for example, the aforementioned microprocessor, RAM, ROM, hard disk drive, circuit board, and the like. The storage device such as a hard disk drive stores in advance computer programs that cause the microprocessor to implement the functions described above.

(User Interface)

A user interface 240 includes the display 240A and an operation part 240B. The display 240A includes the aforementioned display of the arithmetic and control unit 200 and the display 3. The operation part 240B includes the aforementioned operation device of the arithmetic and control unit 200. The operation part 240B may include various types of buttons and keys provided on the case of the fundus imaging apparatus 1 or the outside. For example, if the fundus camera unit 2 has a case similar to that of a conventional fundus camera, the operation part 240B may include a joy stick, an operation panel, and the like provided to the case. Besides, the display 240A may include various types of displays such as a touch panel and the like arranged on the case of the fundus camera unit 2.

Note that the display 240A and the operation part 240B need not necessarily be formed as separate devices. For example, a device like a touch panel having a display function integrated with an operation function can be used. In such cases, the operation part 240B includes the touch panel and a computer program. The content of operation on the operation part 240B is fed to the controller 210 as an electric signal. Moreover, operations and inputs of information may be performed by using a graphical user interface (GUI) displayed on the display 240A and the operation part 240B.

In the light source unit 120 illustrated in FIG. 3, optical members from the optical fiber 126 to the detector 141, including the clock generating optical system 130, correspond to an example of "clock generator" of the embodiment. The sampling part 162 or the DAQ 160 corresponds to "acquisition part" of the embodiment.

[Operation Example]

Described below is an example of the operation of the fundus imaging apparatus 1.

Figure 7:
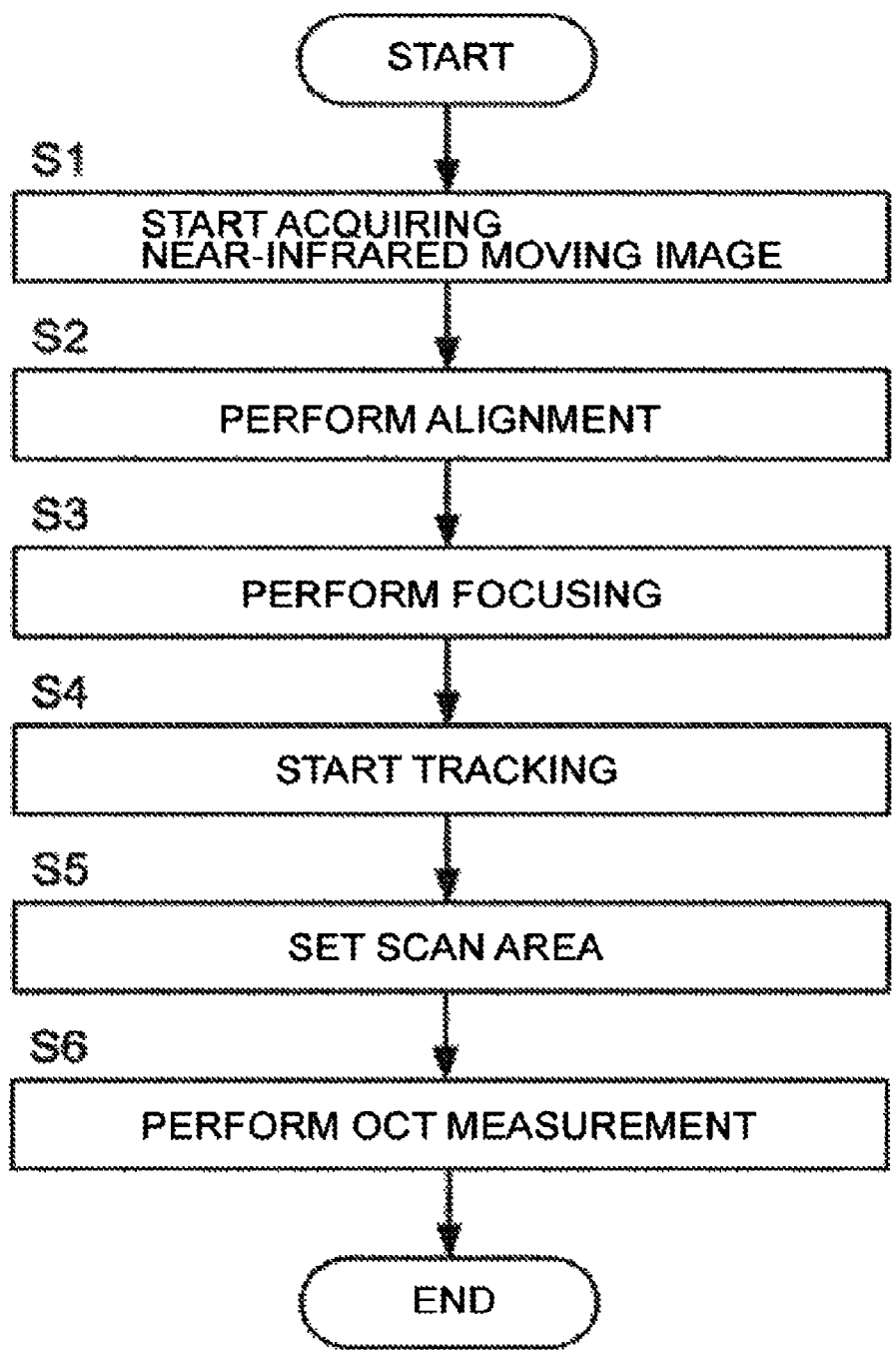
FIG. 7 is a flowchart of an example of the operation of the OCT apparatus of the embodiment.

FIG. 7 is a flowchart illustrating an example of the operation of the fundus imaging apparatus 1. This operation example includes position matching between the eye E and the optical system of the apparatus based on an image and setting of a scan area based on an image. The position matching includes alignment (automatic alignment), focusing (automatic focusing), and tracking (automatic tracking) for OCT measurement.

(S1)

First, the fundus Ef is continuously irradiated with the illumination light from the observation light source 11 (near-infrared light through the action of the visible cut filter 14), thereby starting the acquisition of a near-infrared moving image of the eye E. The near-infrared moving image is acquired in real time until the end of the continuous illumination. The frames of the moving image are temporarily stored in a frame memory (the storage 212) and sequentially sent to the data processor 230.

Incidentally, the alignment indicator and the split target are projected onto the eye E respectively by the alignment optical system and the focus optical system 60. Accordingly, the alignment indicator and the split target are represented in the near-infrared moving image. Alignment and focusing can be performed using them. The fixation target is also projected onto the eye E by the LCD 39. The subject is instructed to fixate the eye on the fixation target.

(S2)

The data processor 230 sequentially analyzes the frames of the moving image of the eye E to find the position of the alignment indicator, thereby calculating the movement amount of the optical system. The controller 210 controls the optical system driver (not illustrated) based on the movement amount of the optical system obtained by the data processor 230 to perform automatic alignment.

(S3)

The data processor 230 sequentially analyzes the frames of the moving image of the eye E to find the position of the split target, thereby calculating the movement amount of the focusing lens 31. The controller 210 controls the focusing driver 31A based on the movement amount of the focusing lens 31 obtained by the data processor 230 to perform automatic focusing.

(S4)

Subsequently, the controller 210 starts the control for automatic tracking. Specifically, the data processor 230 analyzes the frames successively acquired by capturing a moving image of the eye E with the optical system in real time, and monitors the movement (positional change) of the eye E. The controller 210 controls the optical system driver (not illustrated) to move the optical system according to the position of the eye E successively obtained. Thereby, the optical system can follow the movement of the eye E in real time. Thus, it is possible to maintain a good positional relationship with proper alignment and focus.

(S5)

The controller 210 displays the near-infrared moving image on the display 240A in real time. The user sets a scan area on the near-infrared moving image using the operation part 240B. The scan area may be one- or two-dimensional.

If the scan mode of the measurement light LS and a site of interest (optic papilla, macula, lesion, etc.) are set in advance, the controller 210 may set the scan area based on the setting. Specifically, the site of interest is specified by the image analysis of the data processor 230. Then, the controller 210 can set an area in a predetermined pattern to include the site of interest (e.g., such that the site of interest is located in the center).

To set the same scan area as in OCT measurement taken in the past (so-called follow-up), the controller 210 can reproduce and set the past scan area on the real-time near-infrared moving image. As a specific example, the controller 210 stores information (scan mode, etc.) representing the scan area set in the past examination and a near-infrared fundus image (a still image, may be, for example, a frame) in the storage 212 in association with each other (in practice, they are associated also with patient ID and left/right eye information). The controller 210 performs the registration of the past near-infrared fundus image with a frame of the real-time near-infrared moving image, and specifies an image area in the real-time image corresponding to the scan area in the past image. Thereby, the scan area used in the past examination is set in the real-time near-infrared moving image.

(S6)

The controller 210 controls the light source unit 120 and the optical path length changing part 41 as well as controlling the galvano-scanner 42 based on the scan area set in step S5 to perform OCT measurement of the fundus Ef.

As described above, the image forming part 220 forms a cross sectional image of a corresponding A-line based on collected data acquired by sampling detection signals obtained by the detector 150 with reference to a predetermined wavelength position where the reference signal is assigned within a predetermined wavelength sweeping range of the light source unit. If three-dimensional scan is set as the scan mode, the data processor 230 forms a three-dimensional image of the fundus Ef based on a plurality of cross sectional images formed by the image forming part 220. With this, the operation example ends.

Note that the steps S4 and S5 may be performed in reverse order. Besides, in the steps S4 and S5 described above, the near-infrared moving image is displayed, and then a scan area is set thereon. However, the scan area need not necessarily be set in this way. For example, while one frame image (referred to as "reference image") of the near-infrared moving image is being displayed, automatic tracking is performed in the background. When a scan area is set on the reference image, the controller 210 performs registration between the reference image and the image being subjected to the automatic tracking to specify an image area in the real-time near-infrared moving image corresponding to the scan area set on the reference image. Through this process, the scan area can also be set in the real-time near-infrared moving image as in the steps S4 and S5. Further, with this process, the scan area can be set on a still image. This facilitates the setting and increases the accuracy thereof compared to the case of setting the scan area on a moving image being subjected to automatic tracking.

Figure 8:
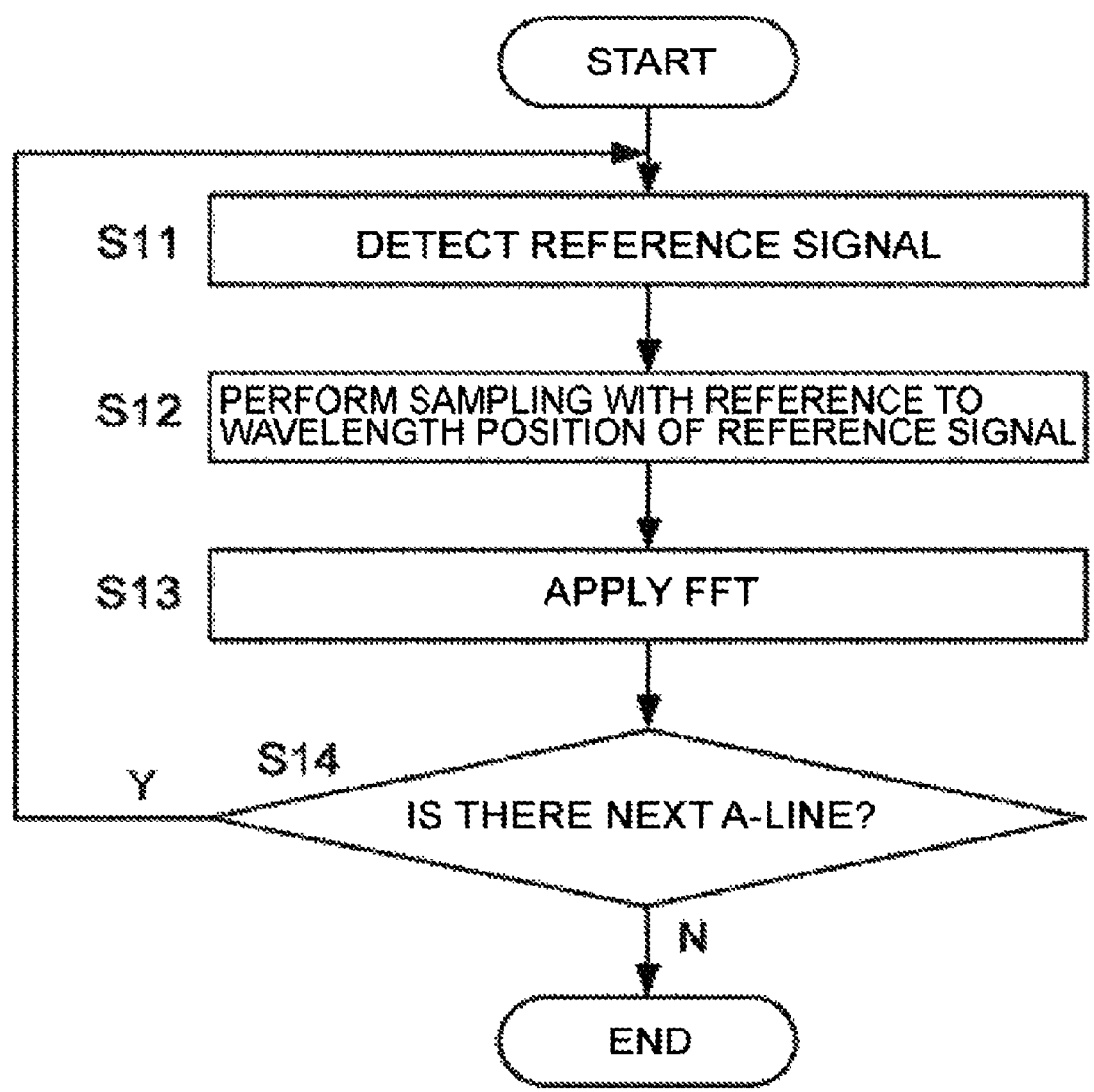
FIG. 8 is a flowchart of an example of the operation of the OCT apparatus of the embodiment.

FIG. 8 is a flowchart illustrating an example of the OCT measurement (S6) in FIG. 7.

(S11)

The detecting part 161 of the DAQ 160 detects the reference signal by comparing the wave height or amplitude of the wavenumber clock KC with a threshold. The detecting part 161 specifies the wavelength position where the reference signal detected is assigned.

(S12)

The sampling part 162 of the DAQ 160 performs the sampling of interference signals with reference to the wavelength position where the reference signal detected in step S11 is assigned. For example, the sampling part 162 starts the sampling of detection signals (interference signals) obtained by the detector 150 from a specific wavelength position behind the wavelength position where the reference signal detected in step S11 is assigned. At this time, the sampling part 162 can acquire collected data by sampling the detection signals at the zero-cross points of the wavenumber clock KC.

(S13)

The image forming part 220 applies known FFT and the like to the collected data of the A-line sampled by the DAQ 160 in step S12.

(S14)

For example, on completion of the process for all A-lines (1024 lines) that constitute a B-scan image (N in step S14), the fundus imaging apparatus 1 ends this operation. On the other hand, if the process has not been completed for all A-lines (Y in step S14), looping back to step S11, the DAQ 160 repeats the same process for the next A-line.

When the amplitude components for all pixels of a single cross sectional image is obtained, for example, the image forming part 220 applies a logarithmic transformation to the amplitude component Am obtained by FFT using "$20 \times \log_{10}(Am+1)$". After that, the image forming part 220 determines a reference noise level in the single cross sectional image. Then, with reference to the reference noise level, the image forming part 220 assigns a value in a predetermined range of brightness values to each pixel according to the amplitude component having been subjected to the logarithmic transformation as described above. The image forming part 220 forms an image using the brightness value assigned to each pixel.

[Effects]

The fundus imaging apparatus 1 is an example of the apparatus that uses the OCT apparatus of the embodiment. Described below are the effects of the OCT apparatus of the embodiment.

According to this embodiment, an OCT apparatus acquires collected data with respect to each A-line by swept-source OCT using a wavelength sweeping light source (e.g., the light source 121) having a predetermined wavelength sweeping range. The OCT apparatus includes a clock generator (e.g., the optical members from the optical fiber 126 to the detector 141, including the clock generating optical system 130), a detector (e.g., the detecting part 161), an acquisition part (e.g., the sampling part 162 or the DAQ 160), and an image forming part (e.g., the image forming part 220). The clock generator is configured to generate a clock (e.g., wavenumber clock), which includes a reference signal in a predetermined wavelength position within a predetermined wavelength sweeping range, and the wavenumber of which linearly varies along the time axis. The detector is configured to detect the reference signal in the clock generated by the clock generator. The acquisition part is configured to sequentially perform sampling of collected data based on the clock with reference to the predetermined wavelength position where the reference signal detected by the detector is assigned to acquire the collected data. The image forming part is configured to form an image of a corresponding A-line based on the collected data acquired by the acquisition part.

With this configuration, a clock assigned a reference signal as a trigger signal is generated, and the sampling of collected data is performed using the clock. This eliminates the need of a conventional trigger signal, thereby reducing the influence of jitter with a simple structure.

The clock generator may include a clock generating optical system (e.g., the clock generating optical system 130) configured to generate a clock based on light from the wavelength sweeping light source.

With this configuration, a clock is optically generated. Therefore, the sapling of the collected data can be performed based on the clock that is not affected by jitter. Thus, the influence of jitter can be removed with a simple structure.

The clock generator may be configured to assign the reference signal to a reference wavelength position in the clock closer to a sweeping start wavelength than to a sweeping end wavelength of the wavelength sweeping light source.

For example, if the reference wavelength position is located outside the imaging range, the reference signal can be used as a trigger signal of wavelength sweeping for the corresponding A-line. Thus, the collected data can be processed in time series without the control for buffering the data to sort it out and the like.

The acquisition part may be configured to start the sampling from a specific wavelength position posterior to the reference wavelength position.

With this configuration, the specific wavelength position may be used as the start position of the imaging range. Thus, the reference signal can be assigned to the clock without affecting the image quality.

This embodiment is applicable to a data processing method. In this case, a data processing method for processing collected data acquired with respect to each A-line by swept-source OCT using a wavelength sweeping light source having a predetermined wavelength sweeping range includes: detecting a reference signal assigned in advance to a clock, in which the wavenumber linearly varies along the time axis, in a predetermined wavelength position within a predetermined wavelength sweeping range; sequentially performing sampling of collected data based on the clock with reference to the predetermined wavelength position where the reference signal detected is assigned; and forming an image of a corresponding A-line based on the sampled collected data. The clock may be optically generated based on light from the wavelength sweeping light source. The reference signal may be assigned to a reference wavelength position closer to a sweeping start wavelength than to a sweeping end wavelength of the wavelength sweeping light source. The sampling may start from a specific wavelength position posterior to the reference wavelength position.

[Modification]

The above embodiment describes the case of removing the influence of jitter without phase correction based on a reference signal; however, the influence of jitter can be removed by correcting the phase of the interference signal based on the similar wavenumber clock KC as in the above embodiment.

In this modification, without detecting the reference signal in the wavenumber clock KC similar to that of the above embodiment, the DAQ 160 performs the sampling of collected data of an A-line acquired by SS-OCT based on the wavenumber clock KC.

The image forming part 220 corrects the phase of the collected data sampled by the DAQ 160 based on the predetermined wavelength position where the reference signal is assigned. The image forming part 220 forms an image of the A-line based on the collected data, the phase of which has been corrected. For example, the image forming part 220 shifts the phase of the wavenumber clock KC with reference to the reference signal to correct the phase of the collected data. Alternatively, the image forming part 220 may shift the phase of the sampled collected data to correct the phase of the collected data.

According to this modification, although there is a need for structure and control to correct the phase of the collected data, no conventional trigger signal is required. Thus, the influence of jitter can be reduced as compared to the conventional technology.

Otherwise, this modification is similar to the above embodiment, and no further description is thought necessary.

[Effects]

Described below is the effects of the OCT apparatus of the modification.

According to the modification, an OCT apparatus acquires collected data with respect to each A-line by swept-source OCT using a wavelength sweeping light source having a predetermined wavelength sweeping range. The OCT apparatus includes a clock generator (e.g., optical members from the optical fiber 126 to the detector 141, including the clock generating optical system 130), an acquisition part (e.g., the sampling part 162 or the DAQ 160), and an image forming part (e.g., the image forming part 220). The clock generator is configured to generate a clock (e.g., wavenumber clock) which includes a reference signal in a predetermined wavelength position within a predetermined wavelength sweeping range, and the wavenumber of which linearly varies along the time axis. The acquisition part is configured to perform sampling of collected data based on the clock generated by the clock generator to acquire the collected data. The image forming part is configured to correct the phase of the collected data acquired by the acquisition part based on the predetermined wavelength position where the reference signal is assigned, and form an image of a corresponding A-line based on the collected data, the phase of which has been corrected.

With this configuration, as in the above embodiment, a clock assigned a reference signal as a trigger signal is generated. This eliminates the need of a conventional trigger signal, thereby reducing the influence of jitter with a simple structure.

This modification is applicable to a data processing method. In this case, a data processing method for processing collected data acquired with respect to each A-line by swept-source OCT using a wavelength sweeping light source having a predetermined wavelength sweeping range includes: performing sampling of collected data based on a clock, which is assigned in advance a reference signal in a predetermined wavelength position in a predetermined wavelength sweeping range, and the wavenumber of which linearly varies along the time axis; correcting the phase of the sampled collected data based on the predetermined wavelength position where the reference signal is assigned; and forming an image of a corresponding A-line based on the collected data, the phase of which has been corrected.

<Other Modifications>

The embodiments described above are mere examples for embodying or carrying out the present invention, and therefore susceptible to several modifications and variations (omission, substitution, addition, etc.), all coming within the scope of the invention.

In the above embodiment and the modification thereof, FBG is provided on the optical path of one of a pair of interference light beams generated by the fiber coupler, and the reference signal is assigned in a desired wavelength position by the other interference light beam and the light having passed through the FBG. However, this is not a limitation. For example, branch light generated by splitting the light L0 from the light source 121 may be guided to the FBG via a circulator to assign the reference signal to a desired wavelength position by light reflected from the FBG.

In the above embodiment and the modification thereof, the difference in optical path length between the optical path of the measurement light LS and that of the reference light LR is varied by changing the position of the optical path length changing part 41; however, the method for changing the difference in optical path length is not limited to this. For example, a reflection mirror (reference mirror) may be arranged on the optical path of the reference light to change the optical path length of the reference light by moving the reference mirror along the traveling direction of the reference light, thereby changing the difference in optical path length. Besides, the optical path length of the measurement light LS may also be changed by moving the fundus camera unit 2 and/or the OCT unit 100 relative to the eye E, thereby changing the difference in optical path length. In addition, if the object to be measured is not a site of a living body, the difference in optical path length may be changed by moving the object in the depth direction (z direction).

A computer program for realizing the above embodiment and the modification thereof may be stored in an arbitrary recording medium that is readable by a computer. Examples of the recording medium include a semiconductor memory, an optical disk, a magneto-optical disk (CD-ROM, DVD- RAM, DVD-ROM, MO, etc.), a magnetic storage medium (a hard disk, a floppy disk (registered trade mark), ZIP, etc.), and the like.

The program may be sent/received through a network such as the Internet or LAN.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A data processing method for processing collected data acquired with respect to each A-line by swept-source OCT using a wavelength sweeping light source having a predetermined wavelength sweeping range, the method comprising:
    detecting a reference signal assigned in advance to a first clock, wavenumber of which linearly varies along a time axis, in a predetermined wavelength position within the predetermined wavelength sweeping range, the first clock being generated based on a branch light obtained by splitting a light from the wavelength sweeping light source, the reference signal being generated by transmitting a part of the first clock to a fiber Bragg grating having a Bragg wavelength corresponding to a wavelength in the predetermined wavelength position, and a second clock is generated by superimposing the reference signal generated using the fiber Bragg grating onto the first clock, and the second clock is sent to a detecting side, and the reference signal is detected from the second clock;
    sequentially performing sampling of the collected data based on the first clock with reference to the predetermined wavelength position where the reference signal detected is assigned; and
    forming an image of a corresponding A-line based on the sampled collected data.

2. A data processing method for processing collected data acquired with respect to each A-line by swept-source OCT using a wavelength sweeping light source having a predetermined wavelength sweeping range, the method comprising:
    performing sampling of the collected data based on a first clock, which is assigned in advance a reference signal in a predetermined wavelength position within the predetermined wavelength sweeping range, and wavenumber of which linearly varies along a time axis, the first clock being generated based on a branch light obtained by splitting a light from the wavelength sweeping light source, the reference signal being generated by transmitting a part of the first clock to a fiber Bragg grating having a Bragg wavelength corresponding to a wavelength in the predetermined wavelength position, and a second clock is generated by superimposing the reference signal generated using the fiber Bragg grating onto the first clock, and the second clock is sent to a detecting side, and the reference signal is detected from the second clock;
    correcting phase of the sampled collected data based on the predetermined wavelength position where the reference signal is assigned; and
    forming an image of a corresponding A-line based on the collected data, the phase of which has been corrected.

3. The data processing method of claim 1, wherein the first clock is optically generated based on light from the wavelength sweeping light source.

4. The data processing method of claim 1, wherein the reference signal is assigned to a reference wavelength position closer to a sweeping start wavelength than to a sweeping end wavelength of the wavelength sweeping light source.

5. The data processing method of claim 4, wherein the sampling starts from a specific wavelength position posterior to the reference wavelength position.

6. An OCT apparatus configured to acquire collected data with respect to each A-line by swept-source OCT using a wavelength sweeping light source having a predetermined wavelength sweeping range, the OCT apparatus comprising:
    a clock generator configured to generate a first clock, which includes a reference signal in a predetermined wavelength position within the predetermined wavelength sweeping range, and wavenumber of which linearly varies along a time axis, the first clock being generated based on a branch light obtained by splitting a light from the wavelength sweeping light source, the reference signal being generated by transmitting a part of the first clock to a fiber Bragg grating having a Bragg wavelength corresponding to a wavelength in the predetermined wavelength position, and a second clock is generated by superimposing the reference signal generated using the fiber Bragg grating onto the first clock, and the second clock is sent to a detecting side, and the reference signal is detected from the second clock;
    a detector configured to detect the reference signal in the first clock generated by the clock generator;
    a control processor configured to control sequentially perform sampling of the collected data based on the first clock with reference to the predetermined wavelength position where the reference signal detected by the detector is assigned to acquire the collected data; and
    an image former configured to form an image of a corresponding A-line based on the collected data acquired by the acquisition part.

7. An OCT apparatus configured to acquire collected data with respect to each A-line by swept-source OCT using a wavelength sweeping light source having a predetermined wavelength sweeping range, the OCT apparatus comprising:
    a clock generator configured to generate a first clock, which includes a reference signal in a predetermined wavelength position within the predetermined wavelength sweeping range, and wavenumber of which linearly varies along a time axis, the first clock being generated based on a branch light obtained by splitting a light from the wavelength sweeping light source, the reference signal being generated by transmitting a part of the first clock to a fiber Bragg grating having a Bragg wavelength corresponding to a wavelength in the predetermined wavelength position, and a second clock is generated by superimposing the reference signal generated using the fiber Bragg grating onto the first clock, and the second clock is sent to a detecting side, and the reference signal is detected from the second clock;
    a control processor configured to control performing sampling of the collected data based on the first clock generated by the clock generator to acquire the collected data; and
    an image former configured to correct phase of the collected data acquired by the acquisition part based on the predetermined wavelength position where the reference signal is assigned, and form an image of a corresponding A-line based on the collected data, the phase of which has been corrected.

8. The OCT apparatus of claim 6, wherein the clock generator includes a clock generating optical system configured to generate the first clock based on light from the wavelength sweeping light source.

9. The OCT apparatus of claim 6, wherein the clock generator is configured to assign the reference signal to a reference wavelength position in the first clock closer to a sweeping start wavelength than to a sweeping end wavelength of the wavelength sweeping light source.

10. The OCT apparatus of claim 9, wherein the control processor is configured to start the sampling from a specific wavelength position posterior to the reference wavelength position.

* * * * *